(12) United States Patent
Rose

(10) Patent No.: US 6,258,022 B1
(45) Date of Patent: Jul. 10, 2001

(54) BEHAVIOR MODIFICATION

(76) Inventor: John Edward Rose, 66 Kings Road, Windsor, Berkshire SL4 2AH (GB)

( * ) Notice: Subject to any disclaimer, the term of this patent is extended or adjusted under 35 U.S.C. 154(b) by 0 days.

(21) Appl. No.: 09/214,938

(22) PCT Filed: Jul. 14, 1997

(86) PCT No.: PCT/GB97/01898

§ 371 Date: Jan. 15, 1999

§ 102(e) Date: Jan. 15, 1999

(87) PCT Pub. No.: WO98/02200

PCT Pub. Date: Jan. 22, 1998

(30) Foreign Application Priority Data

Jul. 16, 1996 (GB) .................................................. 9614913

(51) Int. Cl.⁷ .................................................. A61M 21/00
(52) U.S. Cl. .................................................. 600/26; 600/27
(58) Field of Search .................................................. 600/26, 27

(56) References Cited

U.S. PATENT DOCUMENTS 5,425,699   6/1995   Speigel .
5,518,497 * 5/1996   Widjaja et al. .
5,823,932 * 10/1998  Speigel .................................................. 600/26

FOREIGN PATENT DOCUMENTS 0 195 254   9/1986  (EP) .
2 668 370   4/1992  (FR) .

* cited by examiner

*Primary Examiner*—Max Hindenburg
*Assistant Examiner*—Brian Szmal
(74) *Attorney, Agent, or Firm*—Smith-Hill and Bedell

(57) ABSTRACT

Behavior modification of a human subject takes place under hypnosis, when the subject is in a relaxed state. A machine plays back a video or audio recording, during which the subject is instructed to activate a device to create a perceptible stimulation which is linked, through the hypnosis, with a visualization of enhanced or improved performance. After the hypnosis, the user can reactivate the device at will, whenever the improved performance, such as an improved sporting performance, is desired. This will again create the perceptible stimulation and thus induce the required visualization.

10 Claims, 1 Drawing Sheet

BEHAVIOR MODIFICATION

Figure 1:
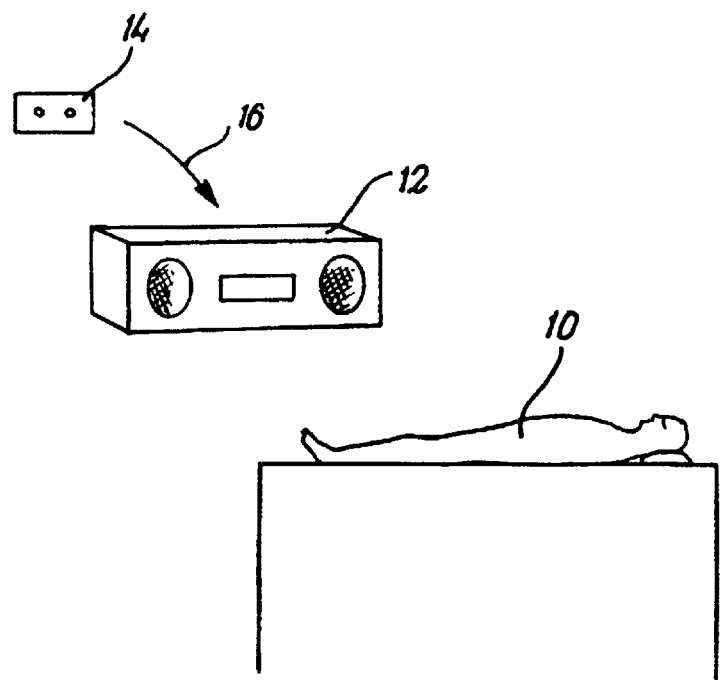

The present invention relates to behaviour modification in human subjects, and particularly, but not exclusively, to performance enhancement.

There are many situations in which the enhancement of human performance is important or desirable. For instance, many sportsmen wish to be able to enhance their performance in order to achieve greater success, but without making use of performance-enhancing drugs or other artificial aids which would infringe rules applicable to their sport or activity. Other desirable types of behaviour modification include overcoming phobias, fear, stress, road rage, insomnia, hypochondria and the like.

The present invention provides a method of behaviour modification of a human subject, in which a visualisation programme is undertaken by the subject under hypnosis and in association with a perceptible stimulation provided by stimulation means, the visualisation programme being so arranged as to enable the subject thereafter, in response to the perceptible stimulation, to visualise modified behaviour.

Preferably the method enhances performance.

The stimulation means is preferably adapted to be activated by the subject, and may be portable. Preferably the stimulation means may be carried or worn by the subject. The stimulation means may provide a stimulation which is perceptible by a part of the subject's body against which the stimulation means is worn or by which the stimulation means is carried or activated. The stimulation means may provide tactile or audible stimulation, such as noise, vibration, mechanical pulses or heat, or any other form of perceptible stimulation, such as trans-dermal, visual, smell, inhalation etc.

The hypnosis may be self-induced or induced externally.

Preferably the visualisation programme includes an induction phase to induce hypnosis, and one or more of the following components:

an ego boosting phase in which the subject is motivated;
a visualisation phase in which modified behaviour is visualised;
an anchoring phase in which a visualisation is anchored to the aforesaid perceptible stimulation; and
a trial phase in which the stimulation means is activated while under hypnosis to recreate a visualisation previously imparted.

Preferably the visualisation programme is pre-recorded, such as by audio or video recording.

The invention also provides stimulation apparatus for use in a method of modifying the behaviour of a human subject, comprising attachment means by which the apparatus may be attached to the body of the subject, and stimulation means operable to provide a stimulation which is perceptible to the subject.

The stimulation means is preferably adapted to be activated by the subject, and may be portable. Preferably the stimulation means may be carried or worn by the subject. The stimulation means may provide a stimulation which is perceptible by a part of the subject's body against which the stimulation means is worn or by which the stimulation means is carried or activated. The stimulation means may provide tactile or audible stimulation, such as noise, vibration, mechanical pulses or heat.

Preferably the stimulation means are mechanical or electrical and may be powered by electrical, mechanical, chemical or solar power means.

The attachment means may comprise a strap and/or adhesive means.

The invention also provides apparatus for behaviour modification, such as performance enhancement, comprising a pre-recorded visualisation programme which, in use, induces hypnosis in a human subject, and stimulation means operable to provide a perceptible stimulation to the human subject, the visualisation programme being so arranged as to enable the subject thereafter, in response to the perceptible stimulation, to visualise modified behaviour.

Preferably the stimulation means is in accordance with one or more definitions of the preceding aspects of the invention.

Preferably the visualisation programme includes an induction phase to induce hypnosis, and one or more of the following components:

an ego boosting phase in which the subject is motivated;
a visualisation phase in which modified behaviour is visualised;
an anchoring phase in which a visualisation is anchored to the aforesaid perceptible stimulation; and
a trial phase in which the stimulation means is activated while under hypnosis to recreate a visualisation previously imparted.

In a further aspect, the invention provides a method of using the apparatus of any of the definitions of the previous aspect of the invention, in which a subject plays back the pre-recorded visualisation programme while exposed to operation of the stimulation means, and wherein the stimulation means is operated by choice by the subject after the visualisation programme has been completed, to re-create, in response to the perceptible stimulation, a visualisation of modified behaviour.

Figure 2:
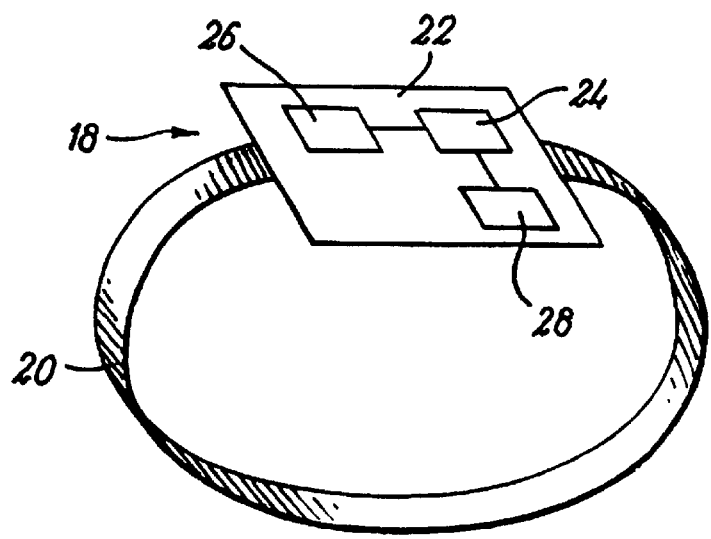

Examples of the present invention will now be described in more detail, by way of example only and with reference to the accompanying drawings, in which:

FIG. 1 is a schematic diagram showing a subject under hypnosis in accordance with the invention; and FIG. 2 is a schematic drawing of a stimulation means for use in accordance with the invention.

FIG. 1 shows a human subject 10 undergoing hypnosis in accordance with the present invention. The hypnosis may be self-induced or externally induced. The subject 10 is in a relaxed state, shown as lying down, preferably in quiet surroundings which may have subdued lighting. The subject 10 is near a machine 12 which can play back a video or audio recording shown schematically as a cassette 14. The cassette 14 is placed into the machine 12 (indicated schematically by the arrow 16) and the programme pre-recorded on the tape is then played back. It is to be appreciated that the recording medium could be any convenient medium, including software, tape, optical or other storage medium.

During playback, the subject 10 is exposed to operation of stimulation apparatus 18 shown generally in FIG. 2. The apparatus 18 has attachment means 20, shown as a strap, by which the apparatus may be attached to the body of the subject 10, such as by strapping the apparatus around the wrist of the subject. The strap 20 carries a capsule 22, preferably sealed against ingress of water, dirt etc. for longevity. Within the capsule 22, there is a power source 24 such as a battery, solar cell, chemical cell or electrical or mechanical power source. This may be renewable or not according to the desired longevity of the device and the capacity of the power source. It is envisaged that a small battery could provide adequate power for many months of normal use, in which case it is envisaged that replenishing the battery would not be necessary, but arrangements could be made for replacing the battery or replenished the power source, if appropriate.

The source 24 provides power for an actuator 26 which provides a tactile or audible stimulation to the subject 10 when actuated. The actuator 26 may provide noise, vibration, mechanical pulses or heat, for instance. By virtue of the strap 20 holding the capsule 22 against the wrist (or other part) of the subject's body, the stimulation provided by the actuator 26 will be perceptible primarily by that part of the subject's body against which the apparatus 18 is worn (with the exception of an audible stimulation).

The capsule 22 also contains a control member 28, such as an electrical switch, operable from outside the capsule 22, such as by finger pressure. When the control 28 is operated, the power source 24 is allowed to operate the actuator 26 to provide the stimulation.

In one alternative, the stimulation may be perceptible by the part of the body by which the control 28 is activated. For instance, a finger pressing on the control 28 may feel a vibration from the actuator 26. Any form of tactile, audio, trans-dermal, visual, smell, inhalation or other stimulation could be used.

The programme pre-recorded on a tape 14 consists of a visualisation programme which includes an induction phase in which hypnosis is induced in the subject, and then further components chosen to create a visualisation programme which enables the subject thereafter (i.e. after completion of the programme) and in response to the perceptible stimulation, to visualise modified behaviour, such as enhanced performance.

In more detail, an example of the visualisation programme would first induce hypnosis, and then take the subject through a sequence of phases including an ego boosting phase in which the user is challenged or motivated to better performance (or modified behaviour such as alleviation of a phobia, fear, stress or other condition) and in which the subject is taught that enhanced performance (or modified behaviour) will be achieved by activation of the stimulation device 18.

The programme then has a visualisation phase in which the subject is encouraged to visualise the improved performance (or modified behaviour) sought, such as a better golf shot, snooker shot, tennis game etc. During this visualisation phase, an anchoring phase occurs in which the subject is instructed to activate the device 18 in order to anchor the visualisation to the perception of stimulation from the apparatus 18. By virtue of the hypnosis, this anchoring imparts in the subject a link between perception of the stimulation and the visualisation, and hence between the stimulation and the modified behaviour or enhanced performance.

There then follows a trial phase in which the stimulation device 18 is activated (while the subject remains under hypnosis) to re-create the visualisation previously imparted.

Finally, the subject is brought back out of hypnosis.

Thereafter, the subject wears the device 18 whenever the activity is being undertaken (such as, during all future golf games). When faced with a difficult situation in which enhanced performance is required, the subject operates the control 28 to provide the stimulation from the actuator 26. By virtue of the connection imparted under hypnosis, the subject will respond to this stimulation by visualising the required enhanced performance, such as a better golf shot, and is then more likely to achieve a better golf shot than would otherwise be the case. The subject does not require any other external assistance in order to re-create this visualisation.

Appendix 1 below sets out in detail an example script for a visualisation programme for use in the manner described.

It is envisaged that the device 18 could be built around devices, known in themselves, which have hitherto been used for producing sound-emitting greetings cards and the like. While primarily intended to produce sound, it is envisaged that commercially known capsules of this nature could be programmed to produce vibration or other mechanical stimulation.

It will be apparent that many variations in the apparatus could be made without departing from the scope of the present invention. In particular, any alternative form of actuation which produces a tactile or audible stimulation could be used, as could any convenient, economic or otherwise appropriate power source and control device. The apparatus could be packaged in order to be worn or attached to any convenient part of the body, although the wrist is preferred. A strap is convenient for attachment to the wrist, but alternatively, or in addition, adhesive securing could be used.

The visualisation programme can be used to enhance performance in any of a wide range of skills and activities, such as sports, pastimes, business or other skills. Although described primarily in relation to performance enhancement in a specific skill, the programme can also be used for general behaviour modification, such as overcoming phobias, fears, stress, road rage, insomnia, hypochondria etc.

Whilst endeavouring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

APPENDIX 1

Introduction

Thank you for purchasing your CAN-DO PATCH. By the purchase of your CAN-DO PATCH you have made a positive statement about yourself and believe this . . . have shown yourself willing to take those positive steps which, with the use of your CAN-DO PATCH will empower you to make changes to your life . . . forever!

You will have read our information leaflet about your CAN-DO PATCH and the process involved and by now I assume you will want to commence to gain the improvements you seek so much.

Induction

Firstly ensure that your CAN-DO PATCH is adhering to a part of your body easily accessible by touch when playing your game.

Now find a place where you can be or sit comfortably without being able to be disturbed by noise or people.

I wonder if you can take two or three deep breaths; really long deep breath, really filling up your lungs and letting the breath out slowly, very slowly . . . just try that now . . . (pause). Excellent . . . you are about to experience with the aid of your mind and your CAN-DO PATCH and enjoy a very positive and beneficial experience . . . and this is true . . . because the things you used to dream about can now (as you continue to breath deeply and slowly) become your reality . . . now become aware of the area around your CAN-DO PATCH and now of all the sounds around you . . . the sound of my voice . . . the music . . . sounds outside . . . and just allow each sound to become a signal . . . a signal for you to relax with. Just disassociate yourself at this moment even from your thoughts . . . The way to do this is to relax completely . . . not only will this relaxation help to remove any anxiety or discomfort from your life but it is a wonderful way of quieting your rational thinking mind which is the verbal part of your nervous system . . . and if images are passing through your mind, just let them . . . just let them go in one side and out the other . . . and by doing so you may find new insights to improve your life . . . or uncover misconceptions about your playing skills . . . so for now just drift and dream . . . feel your feet relaxing . . . The relaxing feeling making your legs heavy as its power moves through your body . . . legs totally relaxed—hips—thighs . . . comfortable all tension leaving your body as its warm relaxing power moves through your spine . . . relaxing your shoulders and arms . . . so easy and heavily relaxed . . . breathing deeper, legs—body—arms—wrists and fingers. Just completely relax as you feel its warmth and relaxation. Relax your neck moving upwards into your scalp—relaxing your scalp—that feeling—breathing deeply . . . into your eyelids—your lids heavy and heavier . . . your face muscles relaxing—loose—downwards—your jaw slack—your teeth parted . . . just good warm feelings . . . going around your mind and body as you continue to enjoy the power of positive relaxation for a moment now just focus on the area around your CAN-DO PATCH and . . . as you continue to relax you may be able to picture dramatic changes in the way you think . . . and you may be doubtful at first but I'm not trying to get you to do the impossible or anything unrealistic . . . I'm only helping you to create . . . to create the changes in your life . . . in your playing skills and your attitude to your game . . . The changes that you desire with skilful use of your CAN-DO PATCH . . . and with some determination . . . and some hard work on your part . . . you can help yourself . . . your game to function more skilfully . . . helping you to fulfil your goals . . . your ambitions.

Egg Boost

The suggestions you hear which are for your benefit . . . your subconscious, will know automatically . . . will, with trained use of your CAN-DO PATCH, create a deep and lasting impression in your mind so deep and lasting that your sub-conscious will use it for your benefit whenever it is necessary: The instructions you hear will begin to exercise a greater and greater influence over you and your game . . . so that the images you will be asked to see will influence the way you concentrate, the way you stand, the way you behave and the way you play. These thing will happen and will remain firmly embedded in the unconscious part of your mind so that from now on they will continue to exercise that same influence over your training . . . over your pre-match strategy . . . over your feelings and above all the excellence of your play when at the event. These influences will remain with you not only during this session but every time your activate your sub-conscious by learning to use your CAN-DO PATCH . . . they will be just as strong . . . just as powerful . . . more so the more you train your mental game using your CAN-DO PATCH . . . the better you will become.

Visualisation and Tactile Anchoring

Now as you continue to relax allow yourself to take another deep breath and again let the breath out slowly and now create a picture in your mind of the game you are in this picture . . . if at first your impressions are a little unclear don't worry because this will improve with practice. See everything in this picture, the colours, the audience, the course, the balls, your opponent . . . notice the smells in the air . . . your opponent, notice how he looks, what he must be feeling . . . take a while to build up this picture putting in as much detail as you are able . . . now see yourself calm . . . confident . . . very cool and very sure of yourself . . . Now activate your CAN-DO PATCH keeping that mental picture of yourself.

Your concentration is one hundred per cent. Your club is an extension of your mind. (Keep your CAN-DO PATCH activated).

Every stroke you play is the best possible.
You see shots well in advance.
You can play the perfect game.
You are calm—cool—concentration intense.
Your shots are controlled and excellent.
You see yourself as a natural winner.

All my suggestions have been communicated into your sub-conscious which will connect each time you use your CAN-DO PATCH.

Trial Run

So one again activate your CAN-DO PATCH and see yourself playing the perfect game . . . you may hear me talking to you as you do this . . . but just play your game in your mind regardless . . . right now . . . (pause).

My concentration is 100%.
My club is an extension of my mind.
My shots are the best possible.
I see shots well in advance.
I play the perfect game.
I am aware calm—confident my concentration intense.
My shots are always controlled and excellent.
I see myself as a natural winner.
. . . (allow 3–5 mins to pass—repeating the above softly)

Excellent—Excellent every part of these suggestions has been noted by your subconscious. From now on every day you will activate your CAN-DO PATCH and visualise your perfect game . . . you will absorb the suggestions contained above as part of your training. Whenever or wherever you are playing . . . when activating your CAN-DO PATCH your images and my suggestions will continue to have a powerful effect on the natural excellence of your game . . . every day and in every way.

Your success is up to you . . . to create the person you can or want to be.

Deep breath now and once more activate your CAN-DO PATCH and bring to mind those positive images . . . repeat along with me . . . silently or aloud . . .
My concentration is 100%.
My club is an extension of my mind.
My shots are the best possible.
I see shots well in advance.
I am always calm, confident . . . concentration intense.
My shots are always controlled and excellent.
I see myself as a natural winner.

Vividly visualise now your game, make all the scenery as real as you are able. Notice how great you feel as you keep your CAN-DO PATCH activated . . . Play now whilst I am quiet (pause 3–5 mins).

Awakening: Boost

In just a moment you will be asked to open your eyes. I shall count from 10–down to 1: When I reach 3 your eyes will open and on number 1 you will feel great, re-energised and full of enthusiasm and confidence about training using your CAN-DO PATCH and future game.

NB

You may like to create difficult situation scenarios whereby in your mind you are able to play superbly to escape and win. Do this and remember to activate your CAN-DO PATCH when you do this.

Whenever you play always activate your CAN-DO PATCH when your need to.

What is claimed is:

1. A method of stimulating enhanced performance of an activity by a human subject, comprising the steps of a) providing a stimulation means for applying a mechanically or electrically operated stimulus, b) hypnotizing the human subject and subjecting him to a visualization program while under hypnosis, c) employing the stimulation means to apply a stimulus to the subject during the visualization program, d) bringing the subject out of hypnosis, and e) employing the stimulation means to reapply said stimulus after hypnosis under the control of the subject during the activity of which performance is to be enhanced.

2. A method according to claim 1, wherein step a) comprises providing a portable stimulation means.

3. A method according to claim 2, wherein step a) comprises providing a stimulation means that is able to be carried or worn by the subject during use.

4. A method according to claim 3, wherein step a) comprises providing a stimulation means that is operable to provide a stimulus that is perceptible by a part of the subject's body against which the stimulation means is worn or by which the stimulation means is carried or activated.

5. A method according to claim 1, wherein step a) comprises providing a stimulation means that applies noise, vibration, mechanical pulses or heat.

6. A method according to claim 1, wherein step b) comprises inducing a state of self-hypnosis or a state of externally-induced hypnosis.

7. A method according to claim 1, wherein step b) comprises subjecting the subject to a program that includes an induction phase to induce hypnosis and one or more of the following components:
   an ego boosting phase in which the subject is motivates;
   a visualization phase in which performance enhancement is visualized;
   an anchoring phase in which a visualization is anchored to the stimulation; and
   a trial phase in which the stimulation means is activated while a subject is under hypnosis to recreate a visualization previously imparted.

8. A method according to claim 1, wherein step b) comprises subjecting the subject to a pre-recorded visualization program.

9. A method according to claim 1, wherein step b) comprises subjecting the subject to a visualization program in the form of an audio or video recording.

10. A method according to claim 1, wherein steps b) and c) comprise playing a pre-recorded visualization program to the subject while employing the stimulation means to apply a stimulus to the subject, and wherein step e) comprises employing the stimulation means to apply said stimulus by choice of the subject after the visualization program has been completed, to recreate, in response to the stimulus, a visualization of modified behaviour.

* * * * *